United States Patent [19]

Matsuda et al.

[11] Patent Number: 6,139,842
[45] Date of Patent: Oct. 31, 2000

[54] DEODORANT COMPOSITION

[75] Inventors: Ryozo Matsuda, Osaka, Japan; Kuniyoshi Torii, 1-1-3-506 Shinohara Obanoyamacho, Nada-ku, Kobe-shi, Japan

[73] Assignee: Kuniyoshi Torii, Kobe, Japan

[21] Appl. No.: 09/122,882

[22] Filed: Jul. 28, 1998

[30] Foreign Application Priority Data

Apr. 10, 1998 [JP] Japan .................................. 10-116195

[51] Int. Cl.[7] ............................ A61K 35/78; A61K 7/00; A61K 7/32; A61K 7/035; A61K 9/01
[52] U.S. Cl. .......................... 424/195.1; 424/47; 424/65; 424/69; 424/76.1; 514/783
[58] Field of Search .................................. 424/47, 65, 69, 424/76.1, 195.1; 514/783

[56] References Cited

U.S. PATENT DOCUMENTS 4,681,757 7/1987 Mimasu et al. ............................ 424/47

*Primary Examiner*—Shelley A. Dodson
*Attorney, Agent, or Firm*—Millen, White, Zelano & Branigan, P.C.

[57] ABSTRACT

A deodorant composition comprises persimmon fruit juice and an aqueous extract of persimmon leaves in a liquid or solid concentrate form. The composition optionally contains a non-toxic, excipient such as dextrin.

15 Claims, No Drawings

DEODORANT COMPOSITION

BACKGROUND OF THE INVENTION

This invention relates to a deodorant composition for deodorizing living spaces such as toilet rooms and kitchen rooms as well as for deodorizing a variety of commercial products such as food products, cosmetics, textile products and the like.

U.S. Pat. No. 4,681,757 discloses a deodorant composition containing persimmon (Diospyros kaki) fruit juice as an active ingredient. The deodorizing mechanism of this composition is believed to be the ability of various polyphenols and condensed tannins found in the persimmon fruit juice to adsorb or mask various odorants. It was found, however, that the deodorant composition was not fully satisfactory for some applications. The persimmon fruit juice itself has a peculiar odor and generates an odor peculiar to fermented products when allowing spontaneous fermentation. These odors are intolerable when the composition is used in higher concentrations.

A need exists, therefore, for a deodorant composition of the above type which can eliminate or ameliorate the above problem.

SUMMARY OF THE INVENTION

It has now been discovered that an aqueous extract of persimmon leaves not only neutralizes the peculiar and fermentation odor of persimmon fruit juice but also enhances its deodorizing effect when combined with the persimmon fruit juice. Accordingly, the present invention provides a deodorant composition containing persimmon fruit juice and an aqueous extract of persimmon leaves in combination.

DETAILED DISCUSSION

It is known that persimmon leaves contain vitamin C and some flavonoid compounds such as kaempferol and quercetin. It is also known that persimmon leaves have a weak antimicrobial activity. It is believed, therefore, that these and other unidentified substances contained in the persimmon leaf extract are responsible for the above synergistic effect.

Persimmon fruit juice may be prepared and processed as disclosed in U.S. Pat. No. 4,681,757, which is incorporated herein by reference. Preferably, immature or astringent persimmon fruits are crashed and then compressed. The resulting fruit juice is then subjected to spontaneous fermentation in a closed vessel to remove sugar content.

Persimmon leaf extract may be prepared by the conventional method, for example, by extracting dried leaves with a 10% aqueous glycerine solution at about 50° C.

The deodorant composition of the present invention may be prepared by several methods. One method comprises evaporating the fruit juice and the leaf extract separately under reduced pressure to obtain respective concentrates, and then blending them together. The other method, which is most preferable, comprises combining the fruit juice as collected and the leaf extract in a closed vessel, subjecting the mixture to spontaneous fermentation, adding an amount of a non-toxic excipient, and then spray drying the mixture. Preferable examples of excipients usable for this purpose include water-soluble saccharides such as lactose, soluble starch or dextrin. The proportion of each ingredient present in the deodorant composition may vary and generally ranges between about 1 and about 10 parts by weight of persimmon fruit juice per 1 part by weight of persimmon leaf extract in terms of nonvolatiles or evaporation residue.

EXAMPLES

The invention is demonstrated further by the following illustrative examples. Parts and percentage herein are by weight unless otherwise indicated.

Example 1

200 parts of dry persimmon leaves were soaked in 200 parts of 10% aqueous glycerine solution for 24 hours at 50° C. and the leaves were removed by filtering to obtain an aqueous extract of persimmon leaves.

This extract was combined with a juice (about 400 parts) collected from 800 parts of immature persimmon fruits. The mixture was placed in a closed vessel and kept at room temperature for 6 months to allow spontaneous fermentation.

The mixture thus processed was then evaporated under reduced pressure to dryness. About 60 parts of offwhite powder were obtained. This product was used in the deodorizing test in Examples 2 and 3 below.

For comparative purposes, similar dehydration process was repeated starting from persimmon fruit juice alone and persimmon leaf extract alone respectively to obtain a dry concentrate.

Another form of the deodorant composition is produced by adding from 5 to 10 parts of dextrin to 100 parts of the spontaneously fermented mixture of the fruit juice and the leaf extract and then spray drying the mixture incorporating dextrin.

Example 2

The following test specimens were prepared from dry concentrate powders prepared in Example 1.

Specimen A: 3% aqueous solution of the composition of this invention.

Specimen B: 1% aqueous solution of the composition of this invention.

Specimen C: 5% aqueous solution of persimmon fruit juice concentrate.

Specimen D: 5% aqueous solution of concentrated persimmon leaf extract.

A series of 500 ml conical flasks containing 1 ml of each test specimen were provided. To the series of flasks were introduced 500 ppm of ammonia and each of flasks was sealed immediately after the introduction of ammonia and allowed to stand for 30 minutes. Then, the residual concentration of ammonia in the flask was measured using a Kitagawa's gas detector tube. Percent removal of ammonia was then calculated by comparing the residual concentration in the presence of the test specimen with the blank residual concentration measured in the absence of the test specimen.

The same series of tests were carried out by introducing 20 ppm of trimethylamine, 15 ppm of methylmercaptan, 20 ppm of hydrogen sulfide and 20 ppm of isovaleric acid, respectively.

The results are shown in Table 1 below.

TABLE 1

| | Percent Removal of Odorant | | | |
| --- | --- | --- | --- | --- |
| | Specimen | | | |
| Odorant | A | B | C | D |
| Ammonia | 100 | 90 | 75 | 5 |
| Trimethylamine | 100 | 95 | 70 | 10 |
| Methylmercaptan | 100 | 90 | 65 | 0 |
| Hydrogen sulfide | 100 | 95 | 70 | 5 |
| Isovaleric acid | 100 | 90 | 80 | 0 |

As shown in Table 1, the persimmon leaf extract exhibits no or little deodorizing effect when use alone but enhances the deodorizing effect of persimmon fruit juice when combined with it. This is demonstrated by comparing the results between Specimen B and Specimen C. Specimen B containing only 1% of the composition of the invention is more potent in the deodorizing effect than Specimen C containing 5% of concentrated persimmon fruit juice.

Example 3

Three groups of adult healthy testers each comprising 3 males and 3 females were orally given 100 ml of an aqueous suspension containing 0.1% w/v of ground garlic particles and 1% w/v of the composition of the invention (group A), the same volume of an aqueous suspension containing 0.1% w/v of ground garlic particles and 5% w/v of concentrated persimmon fruit juice (group B), and the same volume of an aqueous solution containing 0.1% w/v of ground garlic particles only (control group), respectively. Fifteen hours after the administration, intensities of odor in the breath of tester groups were evaluated by six panelers according to the following scores.

0: Odorless
1: Weakly perceptible to an odor not identified as garlic.
2: Perceptible to slight garlic odor.
3: Perceptible to moderate garlic odor.
4: Perceptible to strong garlic odor.
5: Perceptible to very strong garlic odor.

Table 2 below shows average scores for each group given by individual panelers.

TABLE 2

| Paneler No. | Average score | | |
| --- | --- | --- | --- |
| | Group A | Group B | Control |
| 1 | 0.2 | 0.2 | 4.4 |
| 2 | 0 | 0 | 4.2 |
| 3 | 0 | 0 | 4.0 |
| 4 | 0.2 | 0.4 | 4.2 |
| 5 | 0 | 0.2 | 4.0 |
| 6 | 0.4 | 0.4 | 4.4 |

As shown in Table 2, the deodorizing activity of the composition of the invention is comparable to that of concentrated persimmon fruit juice even at one fifth concentration level.

Example 4

| A granule formulation is prepared according to the following recipe: | |
| --- | --- |
| Deodorant composition of the invention | 3.0 parts |
| Sorbitol | 5.0 parts |
| Orange fruit fiber | 2.0 parts |
| Glucose | 20.0 parts |
| Dextrin | 69.9 parts |
| Flavor | 0.1 parts |
| Total | 100.0 parts |

The above materials are kneaded with a small amount of water, shaped into granules and dried. This preparation is suitable for oral administration for deodorizing mouth or excreted feces.

Example 5

| A spray preparation is formulated according to the following recipe: | |
| --- | --- |
| Deodorant composition of the invention | 1.0 parts |
| Benzalkonium chloride | 1.0 parts |
| Sodium lauryl sulfate | 20.0 parts |
| Purified water | 78.0 parts |
| Total | 100.0 parts |

This preparation is used for deodorizing kitchen waste, shoes cabinets, toilets and the like by spraying.

What is claimed is:

1. A deodorant composition comprising a mixture of persimmon fruit juice and an aqueous extract of persimmon leaves in the form of a liquid concentrate or a dry concentrate.

2. The deodorant composition according to claim 1 wherein the ratio of said persimmon fruit juice to said persimmon leaf extract is from 1:1 to 1:10 by weight as nonvolatiles.

3. The deodorant composition according to claim 1 further comprising a non-toxic excipient selected from saccharides and polysaccharides.

4. The deodorant composition according to claim 3 wherein said excipient is dextrin.

5. A method for preparing a deodorant composition comprising the steps of:

combining persimmon fruit juice and an aqueous extract of persimmon leaves;

subjecting the mixture to spontaneous fermentation in a closed vessel for a sufficient time to substantially remove its sugar content;

adding an amount of a non-toxic excipient selected from saccharides and polysaccharides to said mixture; and spray drying the mixture.

6. The method according to claim 5 wherein said fruit juice is collected from immature persimmon fruits or astringent persimmon fruits.

7. The method according to claim 5 wherein said persimmon leaf extract is prepared by extracting dried persimmon leaves with an aqueous solution of glycerine.

8. The method according to claim 5 wherein said amount of dextrin is from 5 to 10 parts by weight per 100 parts by weight of said mixture.

9. A method for preparing a deodorant composition comprising:

separately subjecting persimmon fruit juice and an aqueous extract of persimmon leaves to evaporation under reduced pressure, thereby generating a concentrate of each; and blending said two concentrates together.

10. The method according to claim 5, wherein said non-toxic excipient is dextrin.

11. The method according to claim 10, wherein said fruit juice is collected from immature persimmon fruits or astringent persimmon fruits.

12. The method according to claim 10, wherein said persimmon leaf extract is prepared by extracting dried persimmon leaves with an aqueous solution of glycerine.

13. The method according to claim 10, wherein said amount of dextrin is from 5 to 10 parts by weight per 100 parts by weight of said mixture.

14. The method according to claim 9, wherein said fruit juice is collected from immature persimmon fruits or astringent persimmon fruits.

15. The method according to claim 9, wherein said said persimmon leaf extract is prepared by extracting dried persimmon leaves with an aqueous solution of glycerine.

\* \* \* \* \*